US00PP26156P2

(12) United States Plant Patent
Psenner

(10) Patent No.: US PP26,156 P2
(45) Date of Patent: Nov. 24, 2015

(54) ***BIDENS* PLANT NAMED 'TOP BID 11904'**

(50) Latin Name: ***Bidens triplinervia*×*Bidens ferulifolia***
Varietal Denomination: TOP BID 11904

(71) Applicant: Thomas Psenner, Eppan (IT)

(72) Inventor: Thomas Psenner, Eppan (IT)

(73) Assignee: Amerinova Properties LLC, Bonsall, CA (US)

( * ) Notice: Subject to any disclaimer, the term of this patent is extended or adjusted under 35 U.S.C. 154(b) by 189 days.

(21) Appl. No.: 13/998,442

(22) Filed: Oct. 31, 2013

(51) Int. Cl.
*A01H 5/02* (2006.01)

(52) U.S. Cl.
USPC ..... Plt./410

(58) Field of Classification Search
USPC ..... Plt./410
See application file for complete search history.

*Primary Examiner* — Anne Grunberg
(74) *Attorney, Agent, or Firm* — C. A. Whealy

(57) ABSTRACT

A new and distinct cultivar of *Bidens* plant named 'TOP BID 11904', characterized by its semi-upright, outwardly spreading and mounding plant habit; vigorous growth habit; relatively large leaves; freely flowering habit; relatively large inflorescences with golden yellow-colored ray florets; and strong peduncles that hold the inflorescences above and beyond the foliar plane.

1 Drawing Sheet

Botanical designation: *Bidens triplinervia*×*Bidens ferulifolia.*

Cultivar denomination: 'TOP BID 11904'.

BACKGROUND OF THE INVENTION

The present invention relates to a new and distinct cultivar of *Bidens* plant, botanically known as *Bidens triplinervia*× *Bidens ferulifolia* and hereinafter referred to by the name 'TOP BID 11904'.

The new *Bidens* is a product of a planned breeding program conducted by the Inventor in Bolzano, Italy. The objective of the breeding program was to develop new *Bidens* plants with large inflorescences with numerous ray florets.

The new *Bidens* plant originated from a cross-pollination made by the Inventor in Bolzano, Italy in May, 2010 of *Bidens triplinervia*×*Bidens ferulifolia* 'BID 719', disclosed in U.S. Plant Pat. No. 22,271, as the female, or seed, parent with *Bidens triplinervia*×*Bidens ferulifolia* 'TOP BID 9304', not patented, as the male, or pollen, parent. The new *Bidens* plant was discovered and selected by the Inventor as a single flowering plant from within the progeny of the stated cross-pollination grown in a controlled environment in Bolzano, Italy in October, 2010.

Asexual reproduction of the new *Bidens* by vegetative cuttings in a controlled environment in Bolzano, Italy since November, 2010, has shown that the unique features of this new *Bidens* plant are stable and reproduced true to type in successive generations.

SUMMARY OF THE INVENTION

Plants of the new *Bidens* have not been observed under all possible environmental conditions and cultural practices. The phenotype may vary somewhat with variations in environmental conditions such as temperature and light intensity, without, however, any variance in genotype.

The following traits have been repeatedly observed and are determined to be the unique characteristics of 'TOP BID 11904'. These characteristics in combination distinguish 'TOP BID 11904' as a new and distinct *Bidens* plant:

1. Semi-upright, outwardly spreading and mounding plant habit.
2. Vigorous growth habit.
3. Relatively large leaves.
4. Freely flowering habit.
5. Relatively large inflorescences with golden yellow-colored ray florets.
6. Strong peduncles that hold the inflorescences above and beyond the foliar plane.

Plants of the new *Bidens* differ from plants of the female parent, 'BID 719', in the following characteristics:

1. Plants of the new *Bidens* are more upright than and not as trailing as plants of 'BID 719'.
2. Plants of the new *Bidens* have larger leaves than plants of 'BID 719'.
3. Plants of the new *Bidens* have larger inflorescences with more ray florets than plants of 'BID 719'.

Plants of the new *Bidens* differ from plants of the male parent, 'TOP BID 9304', in the following characteristics:

1. Plants of the new *Bidens* were not as vigorous as plants of 'TOP BID 9304'.
2. Plants of the new *Bidens* have larger leaves than plants of 'TOP BID 9304'.
3. Plants of the new *Bidens* have larger inflorescences with more ray florets than plants of 'TOP BID 9304'.

Plants of the new *Bidens* can be compared to plants of *Bidens ferulifolia* 'Bidcomtis', disclosed in U.S. Plant Pat. No. 17,326. In side-by-side comparisons conducted in Bolzano, Italy, plants of the new *Bidens* differed from plants of 'Bidcomtis' in the following characteristics:

1. Plants of the new *Bidens* were more upright than plants of 'Bidcomtis'.
2. Plants of the new *Bidens* had larger leaves than plants of 'Bidcomtis'.

3. Plants of the new *Bidens* had larger inflorescences with more ray florets than plants of 'Bidcomtis'.

BRIEF DESCRIPTION OF THE PHOTOGRAPHS

The accompanying photographs illustrate the overall appearance of the new *Bidens* plant. The photographs show the colors as true as it is reasonably possible to obtain in colored reproductions of this type. Colors in the photographs may differ slightly from the color values cited in the detailed botanical description which accurately describe the colors of the new *Bidens* plant.

The photograph at the bottom of the sheet comprises a side perspective view of a typical flowering plant of 'TOP BID 11904' grown in a container.

The photograph at the top of the sheet is a close-up view of typical inflorescences of 'TOP BID 11904'.

DETAILED BOTANICAL DESCRIPTION

The aforementioned photographs and following observations and measurements describe plants grown in one-gallon containers during the spring in an outdoor nursery in Bonsall, Calif. and under cultural practices typical of commercial *Bidens* production. During the production of the plants, day temperatures ranged from about 10° C. to 21° C., night temperatures ranged from 7° C. to 14° C. and light levels ranged from 4,000 to 6,000 foot-candles. Plants were pinched one time at planting and then a second time about three weeks later. Plants were three months old when the photographs and description were taken. In the following description, color references are made to The Royal Horticultural Society Colour Chart, 2007 Edition, except where general terms of ordinary dictionary significance are used.

Botanical classification: *Bidens triplinervia*×*Bidens ferulifolia* 'TOP BID 11904'.

Parentage:

*Female parent.*—*Bidens triplinervia*×*Bidens ferulifolia* 'BID 719', disclosed in U.S. Plant Pat. No. 22,271.

*Male parent.*—*Bidens triplinervia*×*Bidens ferulifolia* 'TOP BID 9304', not patented.

Propagation:

*Type*.—By vegetative cuttings.

*Time to initiate roots, summer*.—About one week at temperatures about 18° C.

*Time to initiate roots, winter*.—About ten days at temperatures about 18° C.

*Time to produce a rooted young plant, summer*.—About three weeks at temperatures about 18° C.

*Time to produce a rooted young plant, winter*.—About four weeks at temperatures about 18° C.

*Root description*.—Medium in thickness to fine, fleshy; white in color.

*Rooting habit*.—Freely branching; dense.

Plant description:

*Plant and growth habit*.—Semi-upright, outwardly spreading to mounding plant habit; vigorous growth habit; freely branching habit with about five to six primary lateral branches, each primary lateral branch with one to two lateral branches developing at each node.

*Plant height*.—About 26 cm.

*Plant diameter or spread*.—About 38 cm.

*Lateral branches*.—Length: About 27 cm. Diameter: About 6 mm. Internode length: About 2.5 cm. Aspect: Initially upright then outwardly spreading forming a mounding plant habit. Strength: Strong; flexible. Texture: Pubescent; minute. Color, developing: Close to 148C. Color, mature: Close to 199A to 199B.

Leaf description:

*Arrangement*.—Opposite, simple; relatively large.

*Length*.—About 7 cm.

*Width, towards the apex*.—About 3.5 cm.

*Width, towards the base*.—About 6 cm.

*Shape*.—Roughly deltoid; deeply dissected.

*Apex*.—Acute.

*Base*.—Attenuate.

*Margin*.—Deeply dissected.

*Texture, upper and lower surfaces*.—Scattered pubescence; minute.

*Venation pattern*.—Pinnate.

*Color*.—Developing leaves, upper surface: Close to 137C. Developing leaves, lower surface: Close to N138B. Fully expanded leaves, upper surface: Close to 137A to 137B; venation, close to 147C. Fully expanded leaves, lower surface: Close to N138B; venation, close to 147C.

*Petiole length*.—About 1.8 cm.

*Petiole diameter*.—About 2 mm.

*Petiole texture, upper and lower surfaces*.—Pubescent; minute.

*Petiole color, upper surface*.—Close to 146D.

*Petiole color, lower surface*.—Close to 147C.

Inflorescence description:

*Appearance and flowering habit*.—Solitary rotate composite inflorescences that are terminal or axillary; inflorescences are positioned above and beyond the foliar plane on strong peduncles; terminal inflorescences face upright and axillary inflorescences face outwardly; freely flowering habit with about 28 to 29 inflorescences developing per lateral branch.

*Fragrance*.—None detected.

*Time to flower*.—Under natural season conditions, plants flower continuously from spring until the fall in Southern California.

*Inflorescence longevity*.—Individual inflorescences last about five to seven days on the plant; disc florets persistent and ray florets are not persistent.

*Inflorescence buds*.—Height: About 1.5 cm. Diameter: About 1.2 cm. Shape: Ovoid. Color: Close to 1A.

*Inflorescence size*.—Diameter: Large, about 3.7 cm. Depth (height): About 1.8 cm to 2 cm. Disc diameter: About 1.1 cm. Receptacle diameter: About 2.2 cm. Receptacle height: About 8 mm. Receptacle color: Close to 147B.

*Ray florets*.—Quantity and arrangement: About ten to twelve arranged in one to two whorls. Length: About 1.8 cm. Width: About 8 mm. Shape: Narrow fan-shape. Apex: Emarginate. Base: Fused into a short tube. Margin: Entire. Texture, upper and lower surfaces: Longitudinally ridged, glabrous; satiny. Color: When opening, upper surface: Close to 13B. When opening, lower surface: Close to 4A. Fully opened, upper surface: Close to 14A. Fully opened, lower surface: Close to 14B.

*Disc florets*.—Quantity and arrangement: About 105 massed at the center of the receptacle. Shape: Tubular; apex dentate. Length: About 1.2 cm. Diameter: About 1 mm. Texture: Smooth, glabrous. Color, when opening: Apex: Close to 13A. Mid-section: Close to 199C.

Base: Close to NN155D. Color, fully opened: Apex: Close to 14A. Mid-section: Close to 153C. Base: Close to 145D.

*Phyllaries*.—Quantity and arrangement: About 24 arranged in about two whorls. Length: About 1 cm. Width: About 2 mm. Shape: Lanceolate. Apex: Acute. Base: Truncate. Margin: Entire. Texture, upper and lower surfaces: Pubescent; minute. Texture, lower surface: Pubescent. Color, upper surface: Close to 147A. Color, lower surface: Close to 147B.

*Peduncles*.—Length, terminal peduncle: About 8.5 cm. Length, second peduncle: About 7.3 cm. Length, third peduncle: About 6 cm. Diameter, all peduncles: About 2 mm. Strength: Strong; flexible. Aspect, terminal peduncles: Upright. Aspect, axillary peduncles: About 30° to 45° from vertical. Texture: Pubescent. Color: Close to 145B.

*Reproductive organs*.—Androecium: Present on both ray and disc florets. Quantity per floret: Five. Filament length: About 2 mm. Filament color: Close to 4A. Anther shape: Lanceolate. Anther length: About 2 mm. Anther color: Close to 200C. Pollen amount: Scarce. Pollen color: Close to 17B. Gynoecium: Only present on disc florets. Quantity per disc floret: One. Pistil length: About 1.1 cm. Stigma shape: Bi-parted. Stigma color: Close to 17A. Style length: About 6 mm. Style color: Close to 145D. Ovary color: Close to 145D.

*Fruits and seeds*.—Fruit and seed development have not been observed on plants of the new *Bidens*.

Disease & pest resistance: Plants of the new *Bidens* have not been shown to be resistant to pathogens and pests common to *Bidens* plants.

Garden performance: Plants of the new *Bidens* have exhibited good tolerance to rain and wind and have been observed to tolerate temperatures from about 1° C. to about 45° C.

It is claimed:

1. A new and distinct *Bidens* plant named 'TOP BID 11904' as illustrated and described.

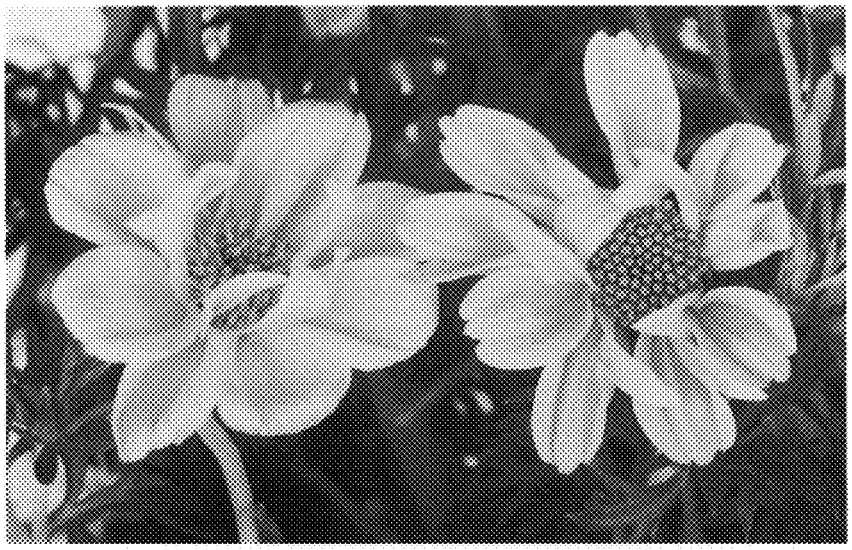
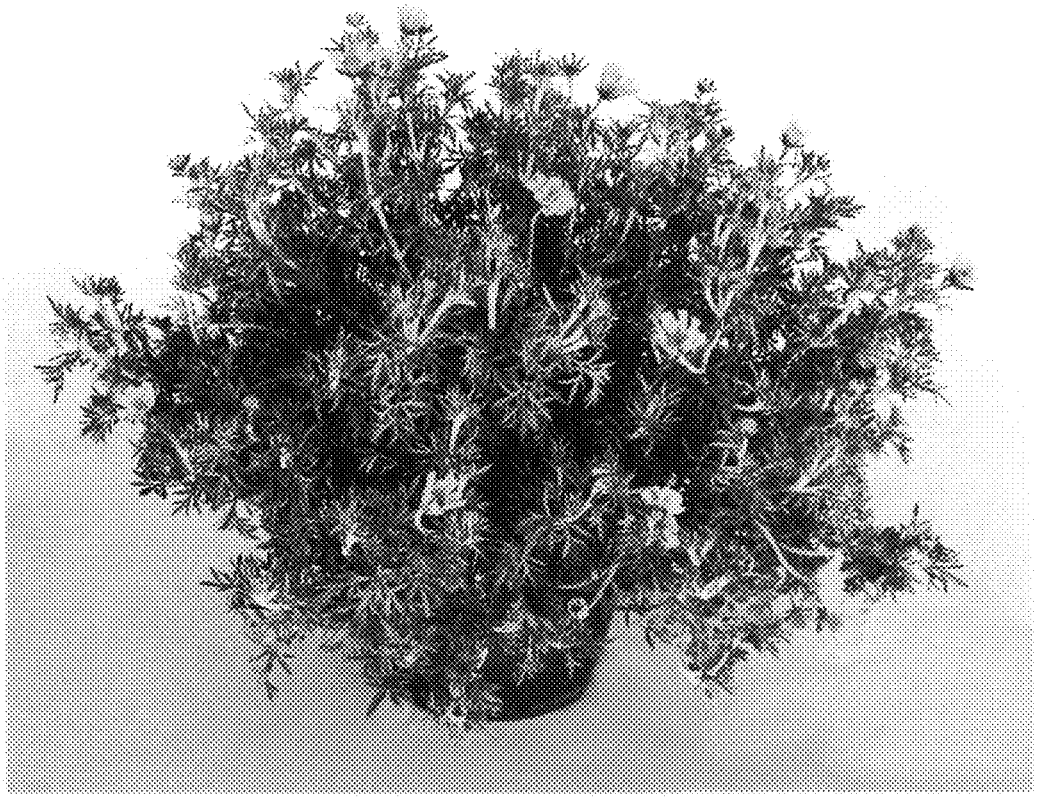

* * * * *